US010244974B2

(12) United States Patent
Garg

(10) Patent No.: US 10,244,974 B2
(45) Date of Patent: Apr. 2, 2019

(54) SINGLE-USE COMPRESSION LANCING DEVICE

(71) Applicant: FACET TECHNOLOGIES, LLC, Atlanta, GA (US)

(72) Inventor: Amit Garg, Atlanta, GA (US)

(73) Assignee: FACET TECHNOLOGIES, LLC, Atlanta, GA (US)

(*) Notice: Subject to any disclaimer, the term of this patent is extended or adjusted under 35 U.S.C. 154(b) by 0 days.

(21) Appl. No.: 15/552,608

(22) PCT Filed: Feb. 19, 2016

(86) PCT No.: PCT/US2016/018599
§ 371 (c)(1),
(2) Date: Aug. 22, 2017

(87) PCT Pub. No.: WO2016/137829
PCT Pub. Date: Sep. 1, 2016

(65) Prior Publication Data
US 2018/0049687 A1    Feb. 22, 2018

Related U.S. Application Data

(60) Provisional application No. 62/119,883, filed on Feb. 24, 2015.

(51) Int. Cl.
*A61B 5/15* (2006.01)
*A61B 5/151* (2006.01)
*A61B 17/34* (2006.01)
*A61B 17/3209* (2006.01)

(52) U.S. Cl.
CPC .. *A61B 5/150412* (2013.01); *A61B 5/150022* (2013.01); *A61B 5/15111* (2013.01); *A61B 5/15144* (2013.01); *A61B 5/150503* (2013.01); *A61B 5/150725* (2013.01); *A61B 5/150748* (2013.01); *A61B 5/150885* (2013.01); *A61B 17/32093* (2013.01); *A61B 2017/3409* (2013.01)

(58) Field of Classification Search
CPC ............... A61B 10/0045; A61B 5/150412
USPC .................. 600/583, 573; 606/181, 182
See application file for complete search history.

(56) References Cited

U.S. PATENT DOCUMENTS 5,540,709 A   7/1996  Ramel
5,908,434 A   6/1999  Schraga
(Continued)

OTHER PUBLICATIONS

International Search Report & Written Opinion for PCT/US2016/018599; dated May 6, 2016; 8 pgs.

*Primary Examiner* — May A Abouelela
(74) *Attorney, Agent, or Firm* — Gardner Groff Greenwald & Villanueva, PC

(57) ABSTRACT

A single-use compression lancing device includes a bottom housing, a top housing, and a lancet. The lancet is generally configured for selective interengagement and guidance within the bottom and top housings. The top housing is configured for slidingly engaging the bottom housing such that manipulation of the top housing relative to the bottom housing causes a sharp tip portion of the lancet to protrude from an opening of the top housing. In one form, at least one arm extending from the lancet interengages a portion of the top housing such that the lancet is retracted within a portion of the bottom housing.

6 Claims, 12 Drawing Sheets

(56) References Cited

U.S. PATENT DOCUMENTS

| | | | |
|---|---|---|---|
| 6,949,111 B2* | 9/2005 | Schraga | A61B 5/150022 606/181 |
| 7,175,641 B1* | 2/2007 | Schraga | A61B 5/15019 606/181 |
| 7,303,573 B2 | 12/2007 | D'Agostino | |
| 7,494,498 B2* | 2/2009 | Lipoma | A61B 5/150022 606/182 |
| 7,955,347 B2 | 6/2011 | Stout | |
| 8,864,783 B2* | 10/2014 | Ruan | A61B 5/1411 606/182 |
| 8,906,055 B2* | 12/2014 | Karbowniczek | A61B 5/1411 606/182 |
| 9,066,688 B2* | 6/2015 | Karbowniczek | A61B 5/1411 |
| 9,743,876 B2* | 8/2017 | Gelfand | A61B 5/15117 |
| 2007/0010841 A1 | 1/2007 | Teo et al. | |
| 2009/0264911 A1* | 10/2009 | Kim | A61B 5/150022 606/182 |
| 2009/0287237 A1* | 11/2009 | Nicholls | A61B 5/150916 606/182 |

* cited by examiner

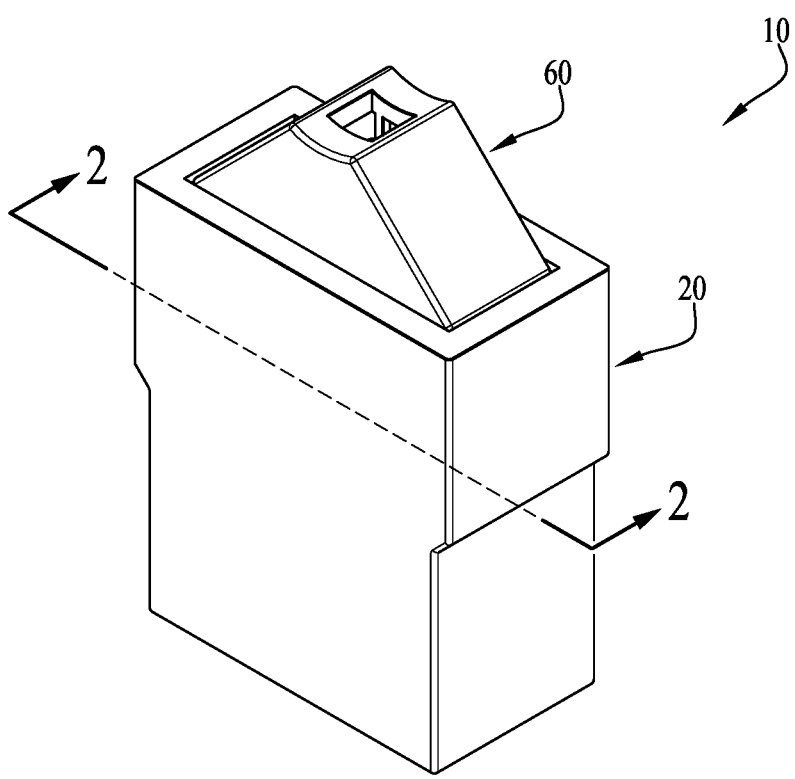
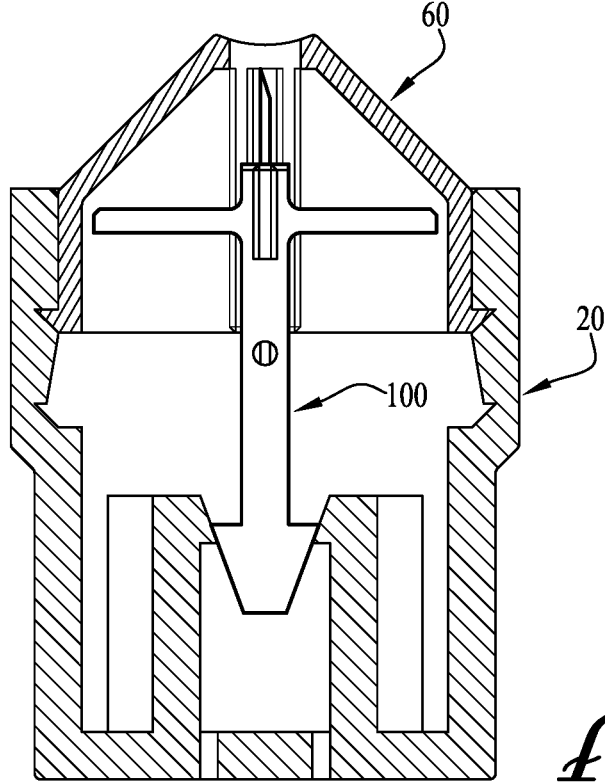

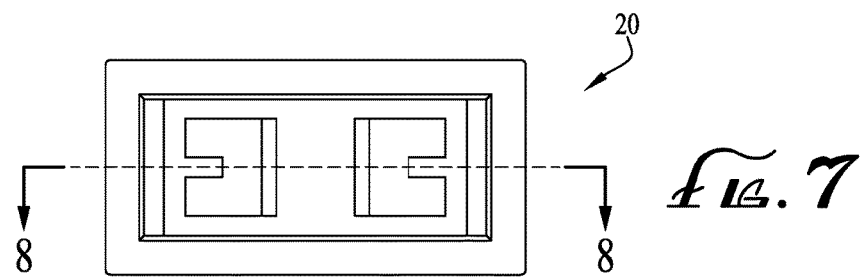
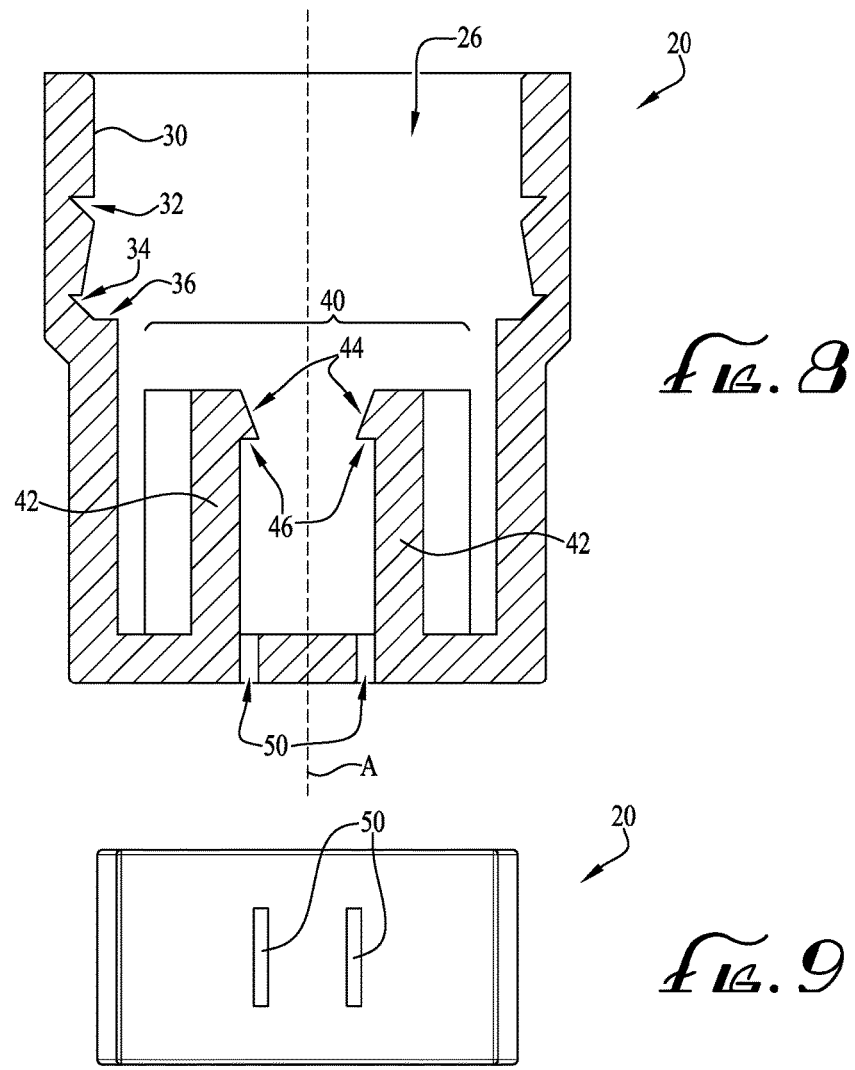

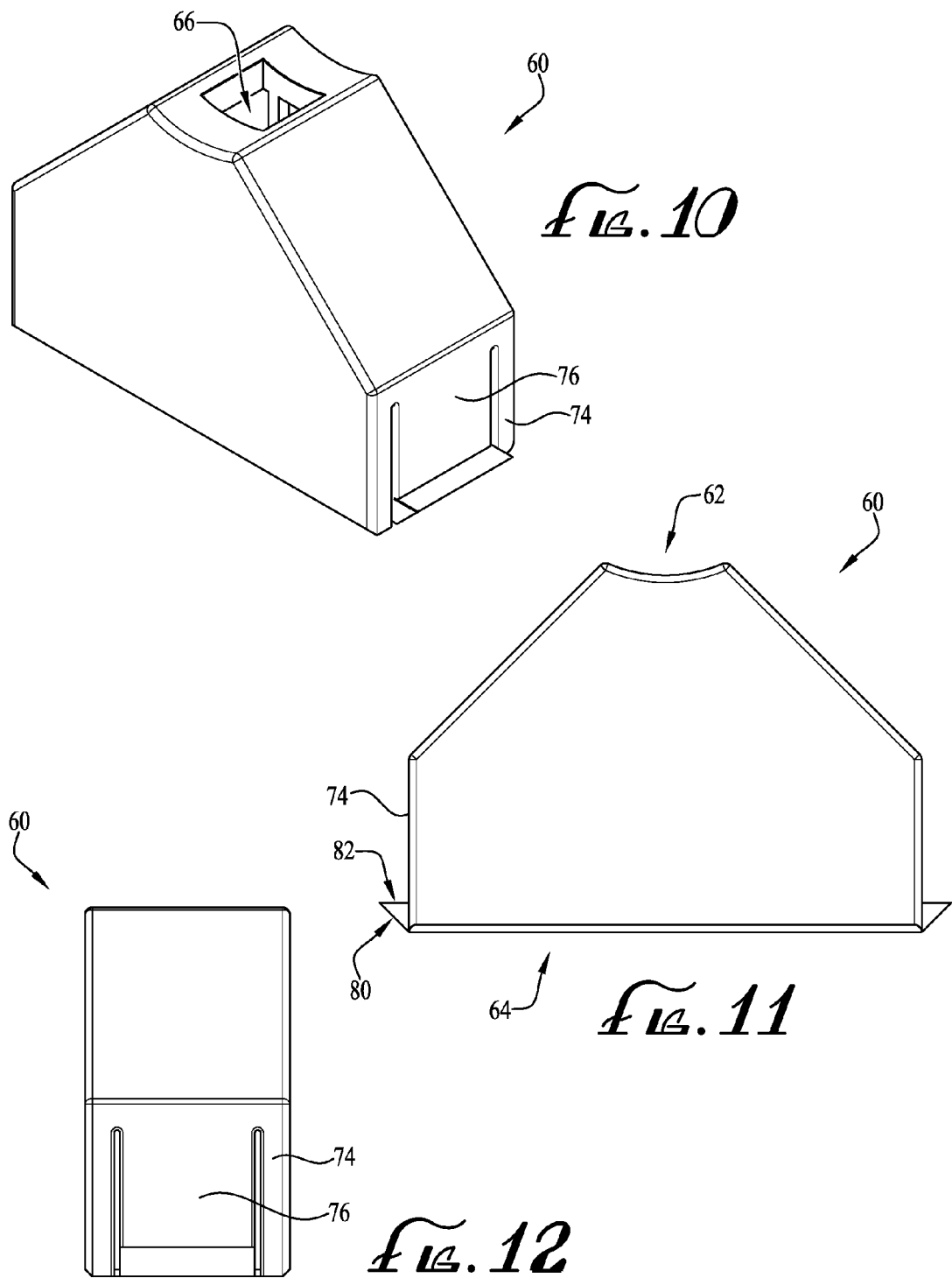

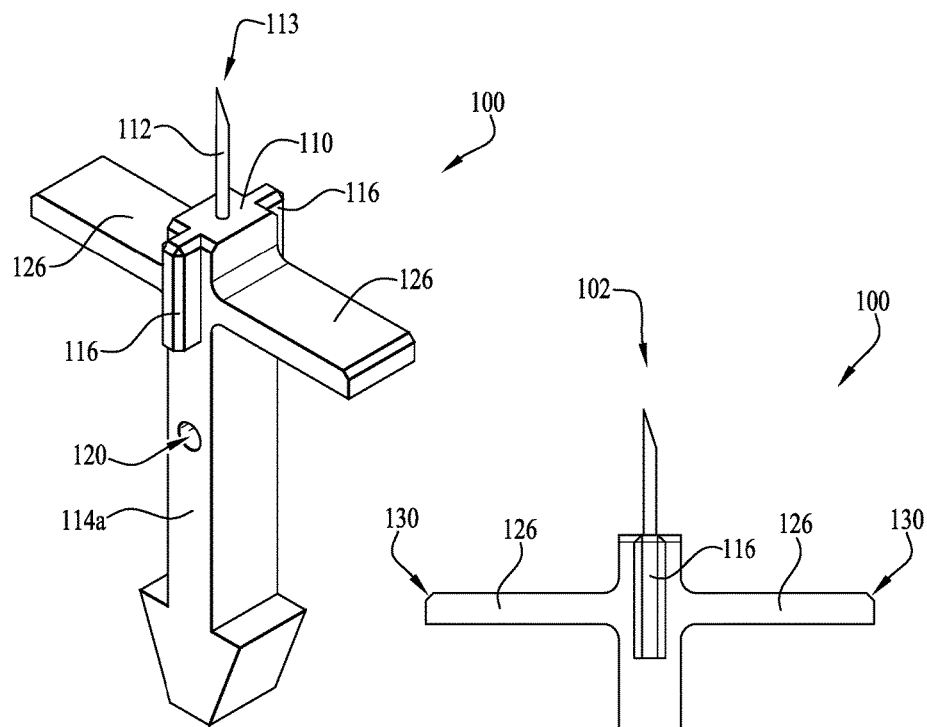
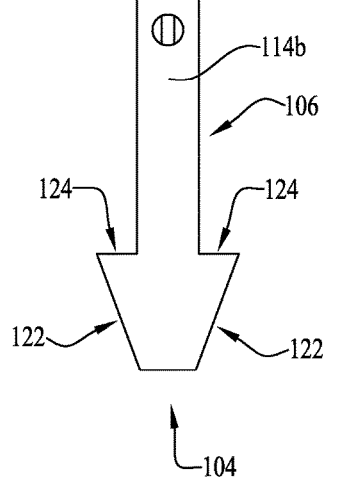

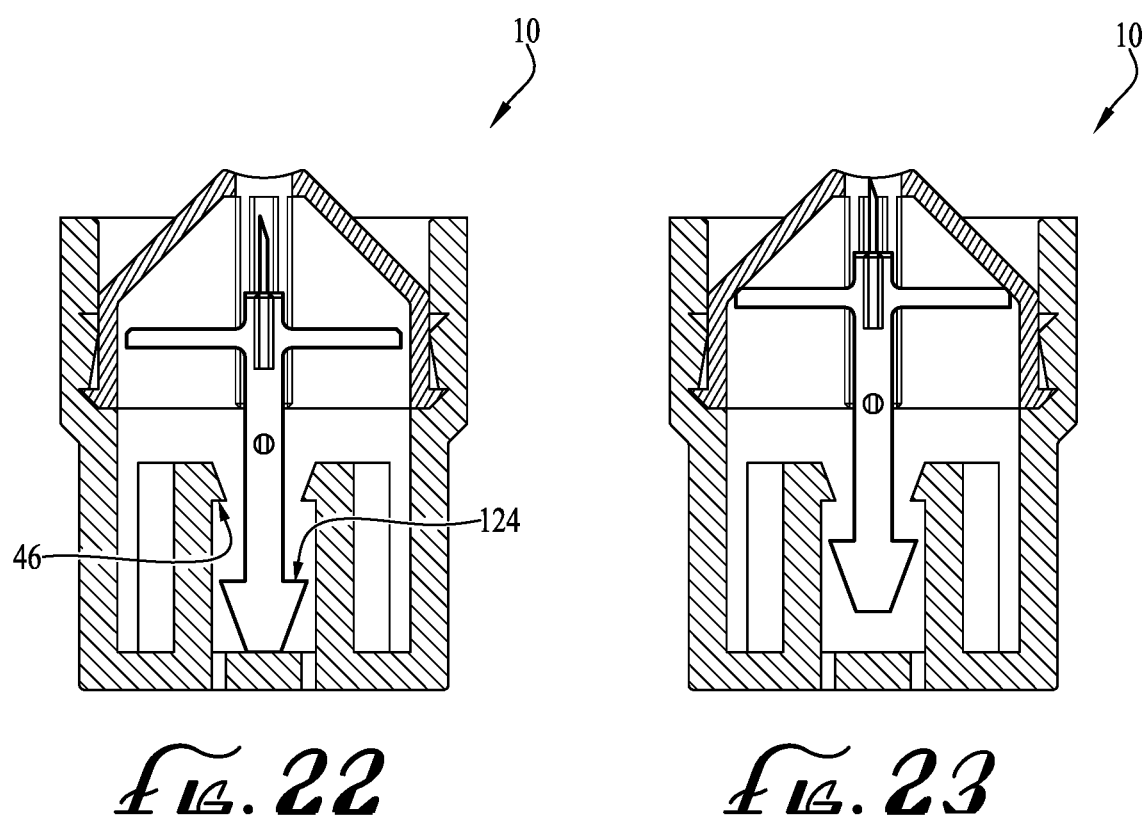

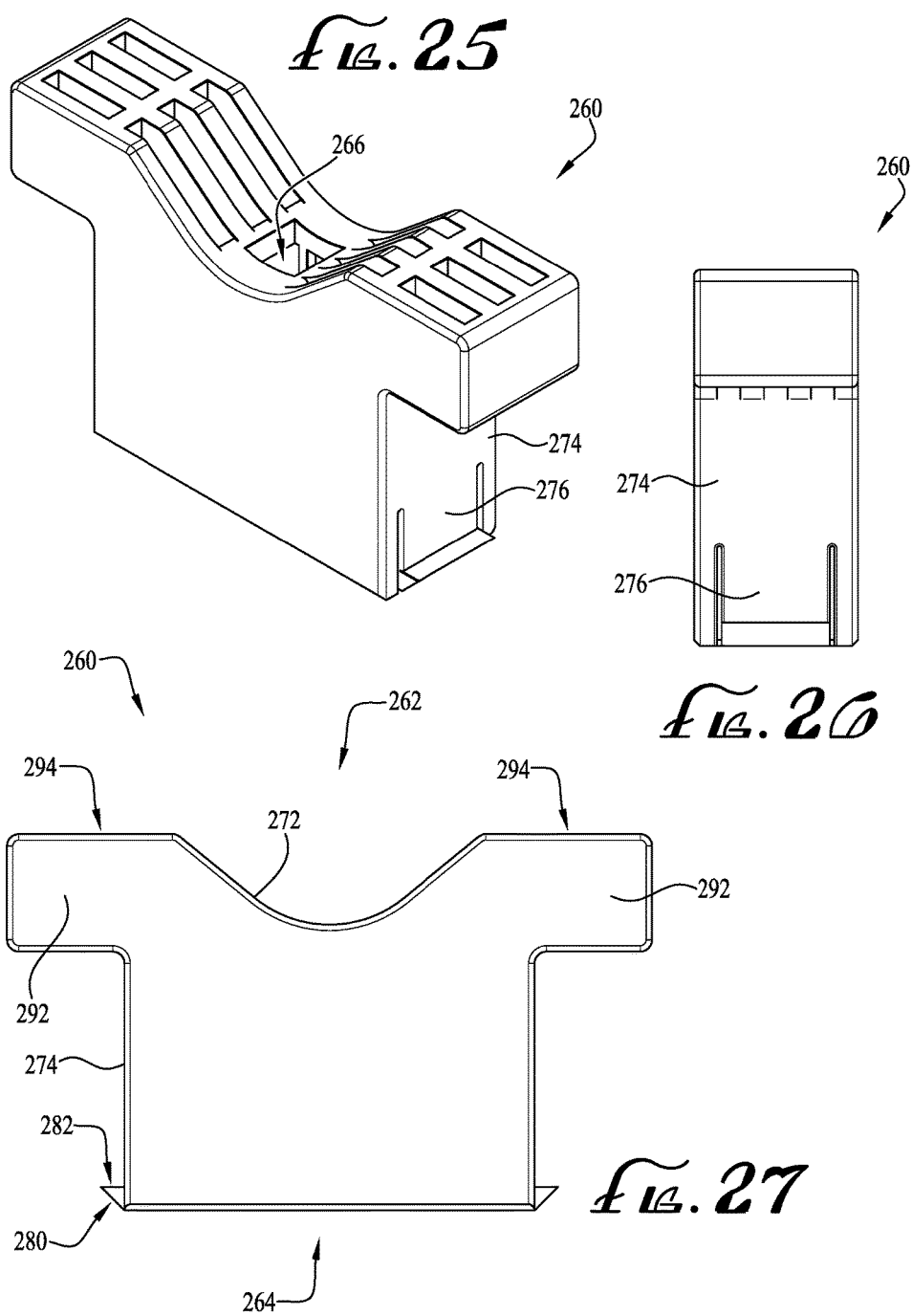

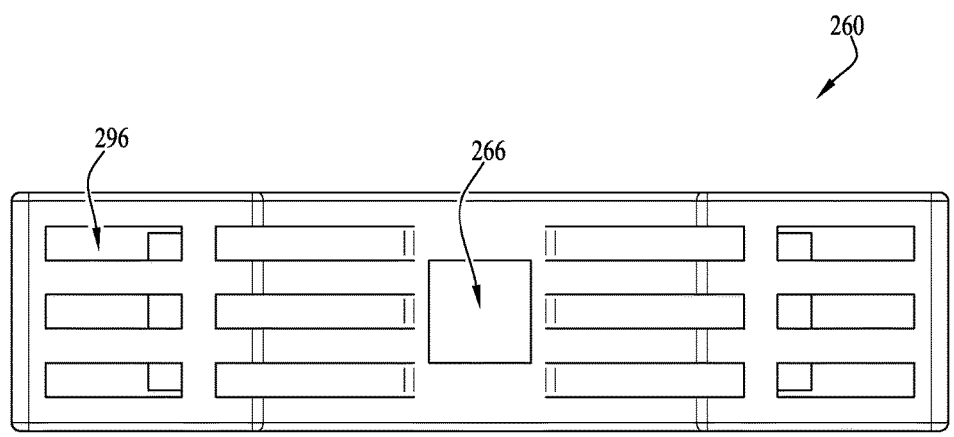
F/G. 28
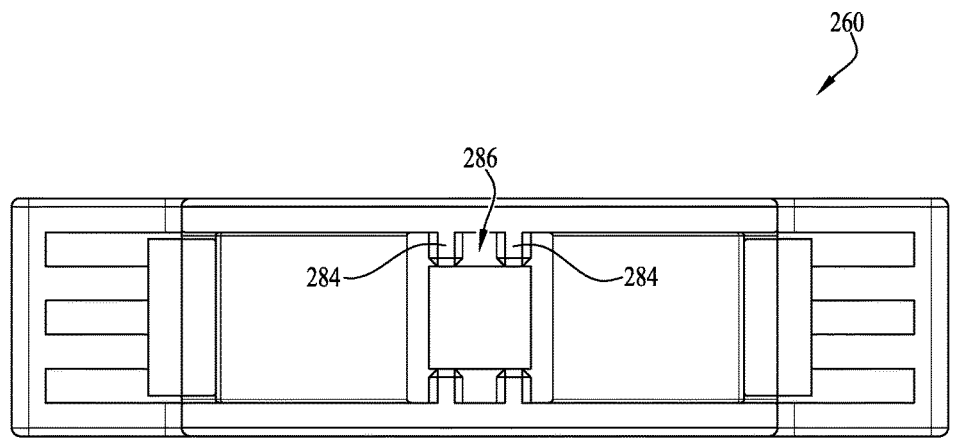
F/G. 29

SINGLE-USE COMPRESSION LANCING DEVICE

CROSS-REFERENCE TO RELATED APPLICATION

This application claims the benefit of U.S. Provisional Patent Application Ser. No. 62/119,883 filed Feb. 24, 2015, the entirety of which is hereby incorporated herein by reference.

TECHNICAL FIELD

The present invention relates generally to the field of medical devices and blood-sampling devices, and more particularly to a single-use compression lancing device.

BACKGROUND

Lancets and lancing devices are utilized for penetrating the skin of a human or animal subject at a lancing site to obtain a sample of blood or other body fluid for medical testing, as in blood-typing or blood-glucose testing. Known lancing devices commonly include a housing containing a drive mechanism, a charging mechanism for energizing the spring or other drive means of the drive mechanism, and a release mechanism for releasing the drive mechanism upon actuation. A lancet is typically propelled by the drive mechanism from a retracted position within the housing to an extended position wherein a sharp tip portion of the lancet projects from the housing to prick the subject's skin at a desired lancing site.

Many lancing devices have a plurality of components including a housing, lancet carrier, drive spring, return spring, actuation trigger, end cap, etc. Typically, the more components a lancing device required, the more costly the product becomes, and the more costly and complex the lancing device is to manufacture and assemble. Accordingly, it can be seen that needs exist for lancing devices having simpler assembly and/or using fewer components, for reducing the cost of production and assembly. It is to the provision of a lancing device meeting these and other needs that the present invention is primarily directed.

SUMMARY

In example embodiments, the present invention provides a single-use compression actuated lancing device including a bottom housing, a top housing, and a lancet. In example forms, with the lancet at least partially inserted within the bottom housing, the top housing is slidingly engaged with the bottom housing. Actuation by compression of the top housing relative to the bottom housing causes movement of the top housing relative to the bottom housing, thereby causing a sharp tip portion of the lancing needed to protrude from an opening of the top housing to prick the skin of a subject. When the top housing is fully pressed within the bottom housing, a pair of arms of the lancet are substantially flexed such that a locking feature of the lancet overcomes the resistance of a lock feature of the bottom housing, thereby causing the flexed arms to cause retraction of the lancet back into the bottom housing.

In one aspect, the present invention relates to a single-use compression lancing device including a lower housing, an upper housing and a lancet. The lower housing extends from a first end to a second end, wherein the first end includes an opening defining a cavity therein. The cavity includes an internal surface and a first locking feature, wherein the internal surface has at least one interengagement feature formed therein. The upper housing extends from a first end to a second end, wherein the first end includes a lancet opening and the second end includes a second opening defining a cavity therein. The lancet opening and the second opening are in communication with the cavity. In one form, at least a portion of the cavity defines an internal surface having an angled wall generally near the lancet opening. The lancet includes a main body portion extending from a first end to a second end, wherein the first end includes a needle extending therefrom and the second end includes a second locking feature for interengagement with the first lock feature. In example forms, at least a portion of the main body includes at least one flexible arm extending therefrom for sliding interengagement with the angled wall of the upper housing.

According to one example form, the upper housing further includes a guidance feature for guiding the lancet along a generally axial path, the guidance feature having at least one ridge defining a channel formed on an internal surface of the cavity. The lancet further includes at least one guide rib for traversing along the channel of the guidance feature. The upper housing further includes side surfaces generally near the second end thereof, and wherein at least one of the side surfaces has a cantilevered finger including a chamfered surface and an overhang. In one form, the cavity of the bottom housing is configured for slidingly receiving the first end of the upper housing, and wherein the chamfered surface and overhang are configured for interengagement with the at least one interengagement feature of the internal surface of the cavity. The top housing is configured to slidingly move within the bottom housing, and wherein the cantilevered finger is configured to removably engage the at least one interengagement feature of the internal surface of the bottom housing. In one form, the top housing is capable of moving relative to the bottom housing in a first direction, but permitted from moving relative to the bottom housing in a second direction, the second direction generally opposite the first direction.

In another aspect, the invention relates to a lancing device including a bottom housing, a top housing, and a lancet. The lancet is generally configured for selective interengagement and guidance within the bottom and top housings, and wherein the top housing is configured for slidingly engaging the bottom housing such that manipulation of the top housing relative to the bottom housing causes a sharp tip portion of the lancet to protrude from an opening of the top housing, and wherein at least one arm extending from the lancet interengages a portion of the top housing such that the lancet is retracted within a portion of the bottom housing.

In example forms, the lancet generally includes a main body portion extending from a first end to a second end. The first end includes a lancet needle projecting therefrom, and the second end includes a locking feature for interengagement with at least one elongate finger extending from an internal portion of the housing generally near a second end thereof. According to example form, manipulation of the top housing relative to the bottom housing causes the at least one resiliently flexible arm extending from the main body portion of the lancet to flex due to contacting an internal wall of the top housing. The locking feature of the second end of the lancet slidingly engages at least one engagement surface of the at least one elongate finger, and wherein when the lancet is in a fully extended state, the at least one resiliently flexible arm is at least partially flexed, and wherein a force generally equal to the force required to at least partially flex the at least one flexible arm forces the locking feature beyond the at least one engagement surface of the at least one elongate finger.

In some example forms, the locking feature of the second end of the lancet includes at least one chamfered engagement surface and at least one lip, and wherein the at least one elongate finger includes at least one chamfered engagement surface and at least one lip. According to example form, the chamfered engagement surfaces and lips of the locking feature and elongate finger, respectively, are configured such that the locking feature of the lancet is capable of moving relative to the at least one elongate finger in a retraction direction, but prevented from moving in a generally opposite lancing direction, whereby the chamfered engagement surfaces slidably engage one another in the retraction direction, and whereby the lips thereof engage each other to prevent a majority of the movement of the lancet relative to the bottom housing in the lancing direction.

These and other aspects, features and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description are exemplary and explanatory of example embodiments of the invention, and are not restrictive of the invention, as claimed.

BRIEF DESCRIPTION OF THE DRAWINGS

FIG. 1 is a perspective view of a single-use compression lacing device according to an example embodiment of the present invention.

FIG. 2 is a cross-sectional view of FIG. 1 taken along line 2-2.

FIGS. 5-9 show front, side, top, bottom and cross-sectional views of the bottom housing of FIG. 4.

FIG. 10 is a perspective view of a top housing of the single-use compression lancing device of FIG. 1.

FIGS. 11-15 show front, side, top, bottom and cross-sectional views of the top housing of FIG. 10.

FIG. 16 is a perspective view of a lancet of the single-use compression lancing device of FIG. 1.

FIG. 17 is a side view of the lancet of FIG. 16.

FIGS. 18-23 show a sequence of operation of the single use compression lancing device of FIG. 1.

FIG. 25 shows a perspective five of the top housing of FIG. 24.

FIGS. 26-29 show side, front, top and bottom views of the top housing of FIG. 25.

DETAILED DESCRIPTION OF EXAMPLE EMBODIMENTS

The present invention may be understood more readily by reference to the following detailed description of example embodiments of the invention taken in connection with the accompanying drawing figures, which form a part of this disclosure. It is to be understood that the invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 3:
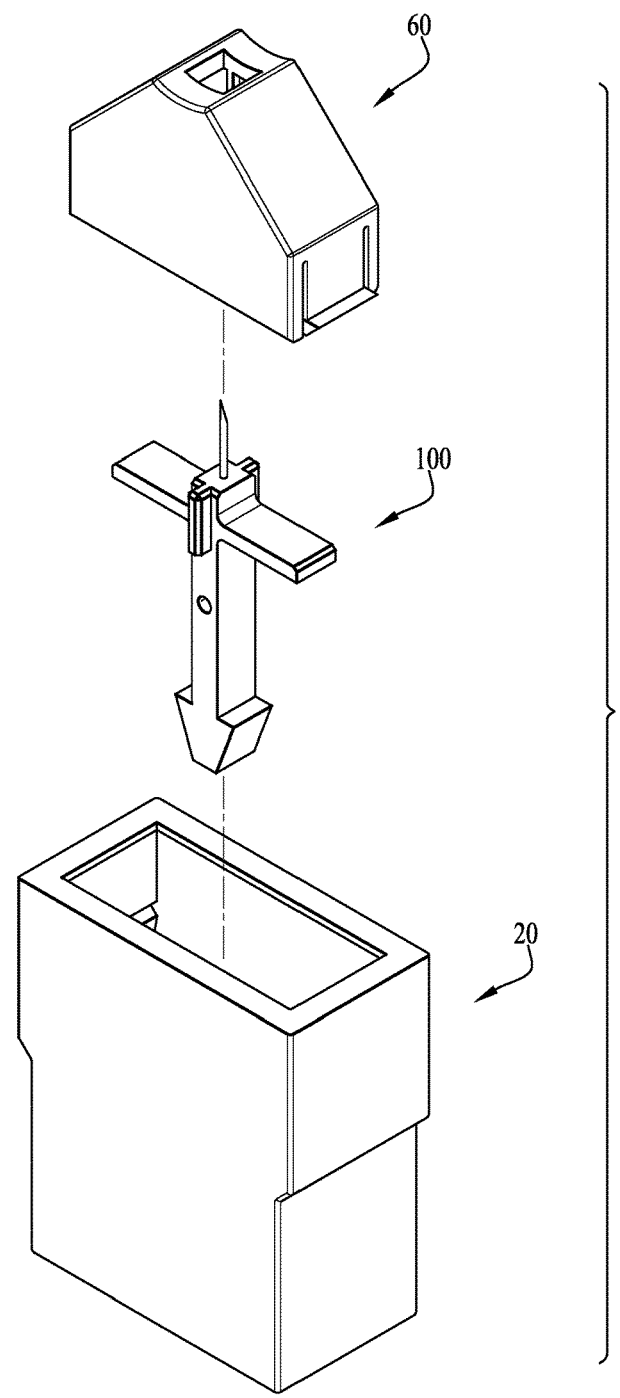
FIG. 3 is an exploded assembly view of the single-use compression lancing device of FIG. 1.

With reference now to the drawing figures, wherein like reference numbers represent corresponding parts throughout the several views, FIGS. 1-3 show a single-use compression lancing device 10 according to an example embodiment of the present invention. As depicted, the lancing device 10 generally comprises a bottom housing 20, a top housing 60, and a lancet 100. Generally, the top housing 60 is configured for sliding engagement with the bottom housing 20, and the lancet 100 is positioned therebetween such that compression of the top housing 60 relative to the bottom housing 20 causes a sharp tip portion 113 and the lancing needle 112 to protrude from an opening 66 of the top housing 60, and then retract within the housings towards a second 24 of the bottom housing 20. In preferred forms, the single-use compression lancing device 10 comprises three components, which are generally separately formed and easily assembled together, thereby decreasing the costs of production and assembly through manufacturing improvements. According to preferred forms, as will be discussed in greater detail below, the lancing device is preferably single-use, whereby once the needle is used one to prick a subject's skin, the lancing device is discarded.

Figure 4:
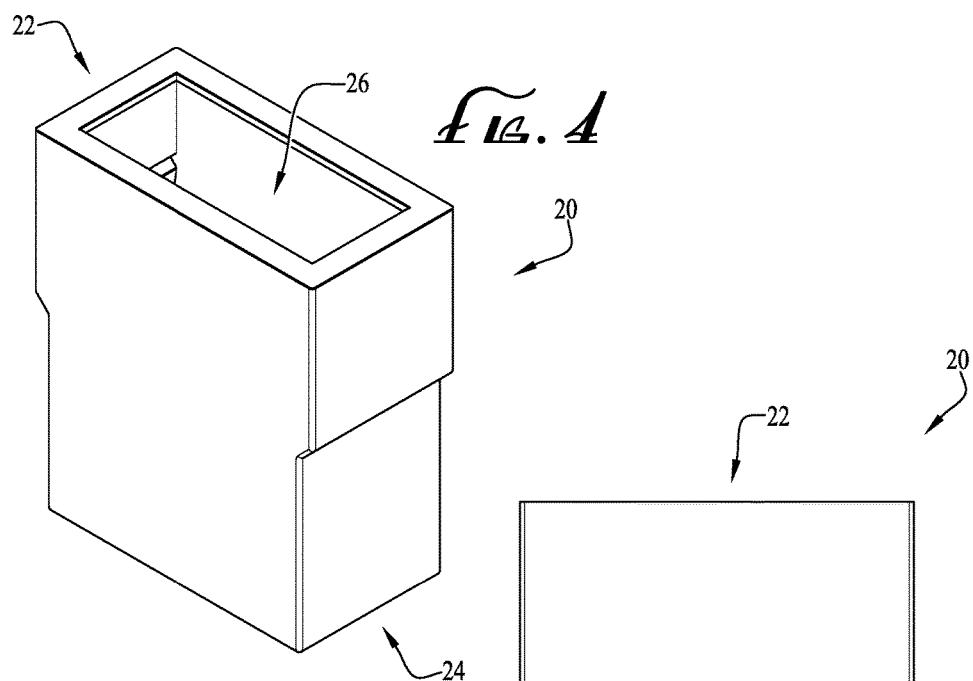
FIG. 4 is a perspective view of a bottom housing of the single-use compression lancing device of FIG. 1.
Figure 5:
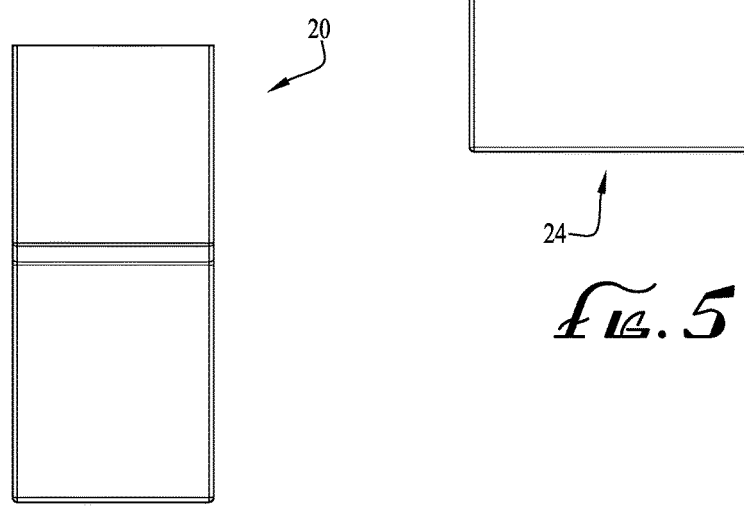
Figure 6:
Figure 13:
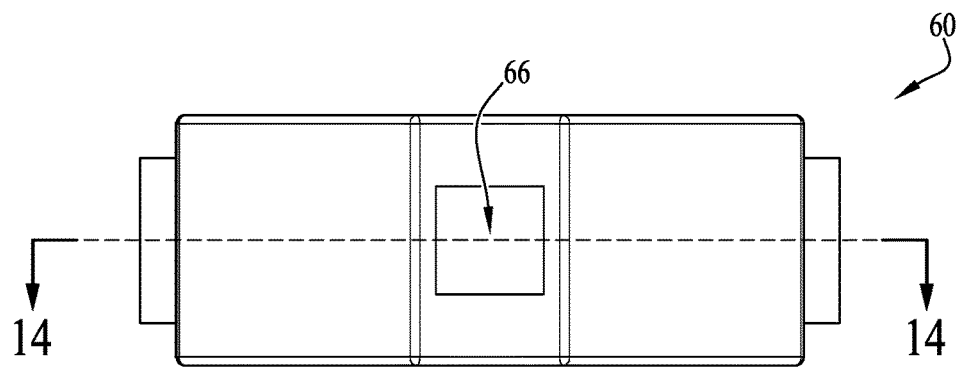

FIGS. 4-9 show the bottom housing 20 in greater detail. As shown in FIGS. 4-6, the bottom housing 20 is generally block-shaped and extends from a first end 22 to a second end 24. The first end 22 defines an opening 26 (having a cavity therein) for receiving the top housing 60 (as will be described below). Alternatively, the bottom housing 20 may be shaped and sized as desired, for example, other shapes including one or more arcuate or curved surfaces, etc. FIGS. 7-9 show additional views of the bottom housing 20 including features thereof found within the cavity.

As shown in FIG. 8, the cavity preferably comprises an interior surface 30 therein wherein one or more interengagement features are formed. For example, generally near the first end 22 of the housing, a pair of first positional indentations 32 are provided, which are generally triangular shaped cutouts formed within the interior surface 30. According to one form, one first positional indentation 32 is provided on one side of the interior surface 30 and another first positional indentation 32 is provided on another (generally opposite) side of the interior surface 30. Typically, the first positional indentations 32 are generally axially aligned along the same horizontal plane. Moving further within the cavity towards the second end 24 of the bottom housing 20, a pair of second positional indentations 34 are provided, which generally comprise a similarly shaped triangular cutout shape. Similarly, the second positional indentations 34 are generally axially aligned along the same horizontal plane, which is generally laterally offset from the horizontal plane of the first positional indentations 32. In one example form, a stop surface 36 is generally provided near the second positional indentation 34.

A lock feature 40 extends from within the cavity near the second end 24 towards the first end 22 for providing interengagement with the lancet 100 (as will be described below). According to one example form, the lock feature 40 comprises a pair of elongate fingers 42, which are generally at least partially flexible and resilient for providing interengagement with a portion of the lancet 100. In preferred example forms, the elongate fingers 42 are generally configured for sliding engagement with a portion of the lancet 100. In one form, the elongate fingers 42 each comprise a chamfered engagement surface 44 and an overhang or lip 46. Preferably, the chamfered engagement surfaces 44 are generally angled or sloped towards each other, for example wherein they are generally symmetric relative to one another in a generally inward and downward position directed at an axis A, which is generally axial with a central axis extending from the first end 22 to the second end 24. Optionally, the engagement surfaces 44 may be shaped and sized as desired. Optionally, one or more openings 50 may be formed within the second end 24 of the bottom housing and extend within the cavity.

FIGS. 10-15 show the top housing 60 in greater detail. In one form, the top housing 60 is generally block-shaped and extends from a first end 62 to a second end 64 and defines an internal cavity therein. In general, the second end 64 of the top housing 60 is configured for sliding engagement with the bottom housing 20, for example, wherein the second end 64 is inserted within the opening 26. Typically, the top housing 60 comprises an opening 66 formed at the first end 62 for permitting the sharp tip portion 113 of the lancet needle 112 to extend therethrough to pick the skin of a subject, and an opening 70 is provided for receiving at least a portion of the lancet 100. Preferably, both of the openings 66, 70 preferably provide access and communicate with the internal cavity. According to some example forms, a concave surface or recess 72 is formed within the top housing at the first end generally near the opening 66 to assist in positioning/placing a finger or other portion of the subject near the opening 66.

FIGS. 10-11 show side surfaces 74 of the top housing 60, which generally comprise at least one cantilevered finger 76 formed therewith. According to example forms, a pair of channels extend along the side surfaces 74 of the top housing 60 to form the cantilevered fingers 76. The cantilevered fingers 76 are preferably resiliently flexible such that at least the free ends thereof are capable of moving relative to the side surfaces 74. In example forms, each of the cantilevered fingers 76 generally comprises a chamfered surface 80 and an overhang or lip 82. Preferably, the cantilevered fingers 76 (including the chamfered surface 80 and lip 82) are configured to slidingly engage the positional indentations 32, 34 of the interior surface 30 of the bottom housing 20.

Figure 14:
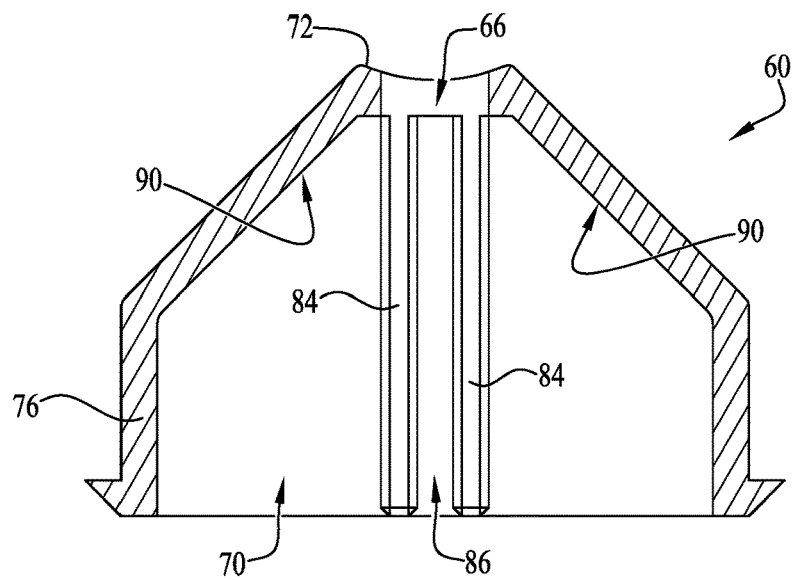
Figure 15:
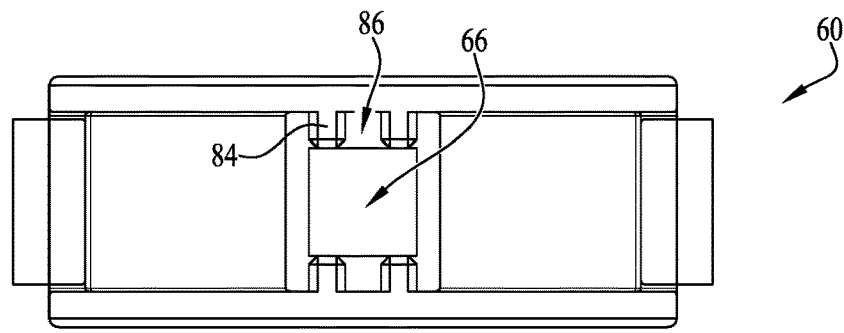

As shown in FIGS. 14-15, at least one ridge 84 and channel 86 is provided within the internal cavity, which generally axially extend from the second end 64 generally proximal the first end 62. According to some form, at least two pairs of ridges 84 (defining a pair of channels 86) are provided within the internal cavity of the top housing 60. Preferably, the at least one ridge 84 and channel 86 provide guidance to the lancet 100. Preferably, at least one internal wall 90 is provided within the internal cavity of the top housing 60 for providing sliding engagement with at least a portion of the lancet 100, as will be described below. According to one form, the internal wall 90 is generally angled towards the opening 66 near the first end 62. Optionally, the internal wall 90 may be shaped and sized as desired. In the depicted embodiment, a pair of opposed internal walls 90 are provided, tapering inwardly toward the opening 66 in a generally symmetric manner, for example at an angle of inclination of about 45°.

FIGS. 16-17 show the lancet 100 in greater detail. The lancet 100 generally comprises a main body portion 106 extending from a first end 102 to a second end 104. An end surface 110 is provided generally near the first end 102 wherein the lancing needle 112 extends therefrom. Preferably, the main body portion 106 comprises generally oppositely-facing side surfaces 114a, 114b. The side surfaces 114a, 114b generally comprise at least one guide rib 116 extending therefrom. The at least one guide rib is preferably provided for being guided by the at least one ridge 84 (within the channel 86 thereof) of the top housing 60. A lancet-holding opening 120 is generally provided along a central portion of the main body portion 106, extending through the side surfaces 114a, 114b for positioning and holding the lancing needle 112 in place when the lancet 100 is manufactured, for example, by injection molding. The second end 104 of the lancet 100 preferably comprises a locking feature for sliding engagement with the lock feature 40 of the bottom housing 20. According to one form, the locking feature generally comprises at least one chamfered surface 122 and at least one overhang or lip 124. In preferred forms, the locking feature comprises a pair of chamfered surfaces 122 and a pair of lips 124. The chamfered surfaces 122 are generally angled downward and inwardly relative to one another.

At least one arm or finger generally transversely extends from the main body portion 106 near the first end 102 thereof. Preferably, the at least one arm 126 is resiliently flexible and spring-like such that engagement with the internal wall 90 of the top housing 60 causes the at least one arm 126 to flex, and whereby when the at least one arm generally extends in a transverse direction relative to the main body portion 106 when not in engagement with the internal wall 90. In some example forms, the at least one arm 126 comprises a chamfered corner 130 for providing sufficient surface-to-surface engagement with the angled internal walls 90 of the top housing 60. In the depicted embodiment, an opposed pair of cantilevered spring arms 126 extend outwardly in opposite directions from the main body portion 106, for example in a generally perpendicular orientation relative to the central main body portion, defining a T-shaped or cross-shaped configuration.

Figure 18:
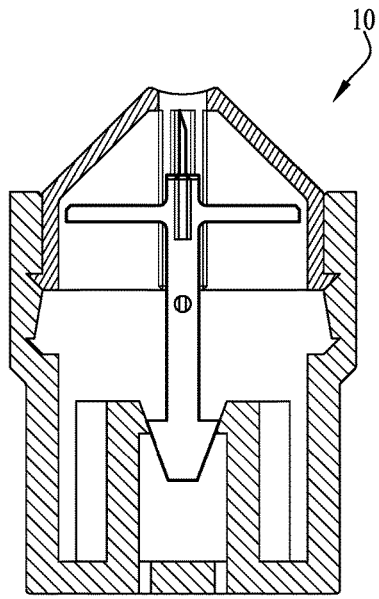
Figure 19:
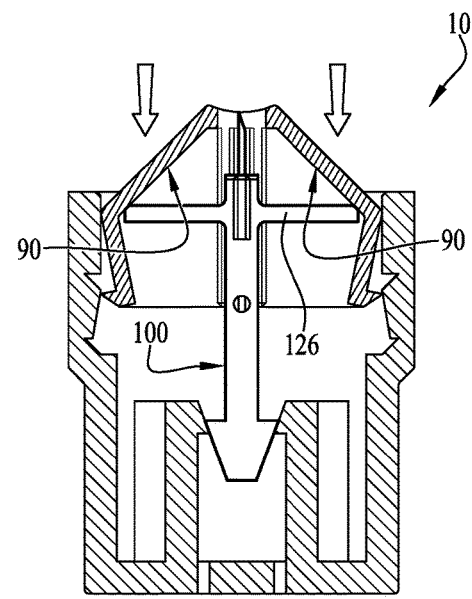
Figure 20:
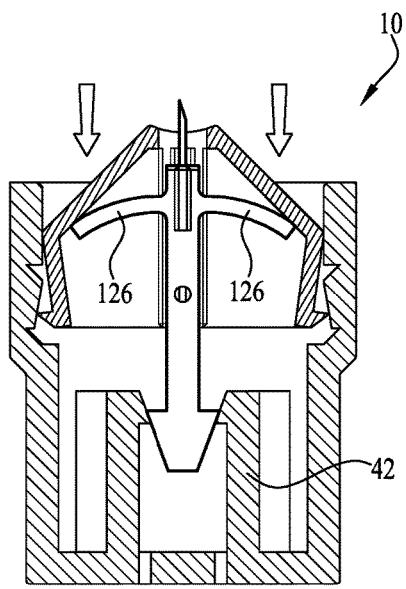

FIGS. 18-23 show a sequence of operation of the lancing device 10. As depicted in FIG. 18, the lancing device 10 is generally in a neutral state wherein the chamfered surfaces 122 of the lancet 100 are contacting the chamfered surfaces 44 of the elongate fingers 42 of the lock feature 40. The second end 64 of the top housing 60 is preferably slidingly engaged within the opening 26 of the bottom housing 20. The cantilevered fingers 76 of the top housing are preferably engaged with the interior surface of the bottom housing 20 such that the chamfered surfaces 80 (and lips 82) are fitted within the first positional indentations 32. To charge and fire the lancing device 10, the top housing 60 is pressed to move further within the bottom housing 20 (see arrows), causing the arms 126 to begin contacting the angled internal walls 90 of the top housing 60 (see FIG. 19). At this stage, the cantilevered fingers 76 are flexed or bent inwardly whereby the chamfered surfaces 80 and lips 82 have become removed from the first positional indentations 32. As the top housing 60 continues to move within the bottom housing 20, the arms 126 begin to flex due to engagement with the angles internal walls 90, for example, since the chamfered surfaces 122 are still contacting the chamfered surfaces 44 of the elongate fingers 42, which prevent the lancet 100 from retracting within the bottom housing 20. The cantilevered fingers 76 eventually reach the second positional indentations 34 such that the chamfered surfaces 80 (and lips 82) are fitted therein, and wherein at least a portion of the cantilevered fingers or an end surface near the second end 64 of the top housing 60 contacts the stop surface 36. Preferably, the needle 112 (and sharp tip portion thereof 113) are projecting from the opening 66 when the cantilevered fingers 76 (including chamfered surfaces 80 and lips 82) reach the second positional indentations 34.

Figure 21:
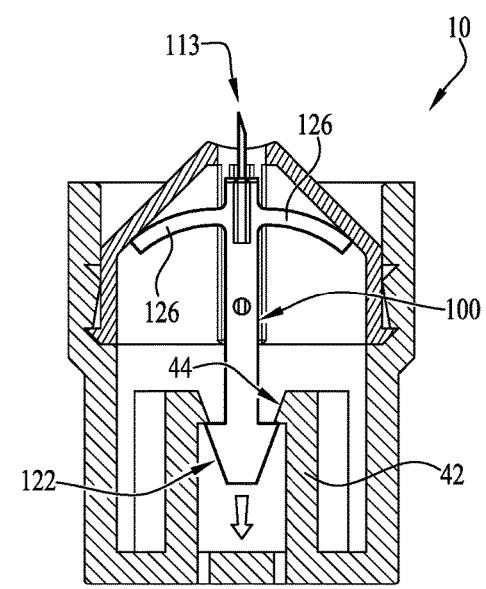
Figure 24:
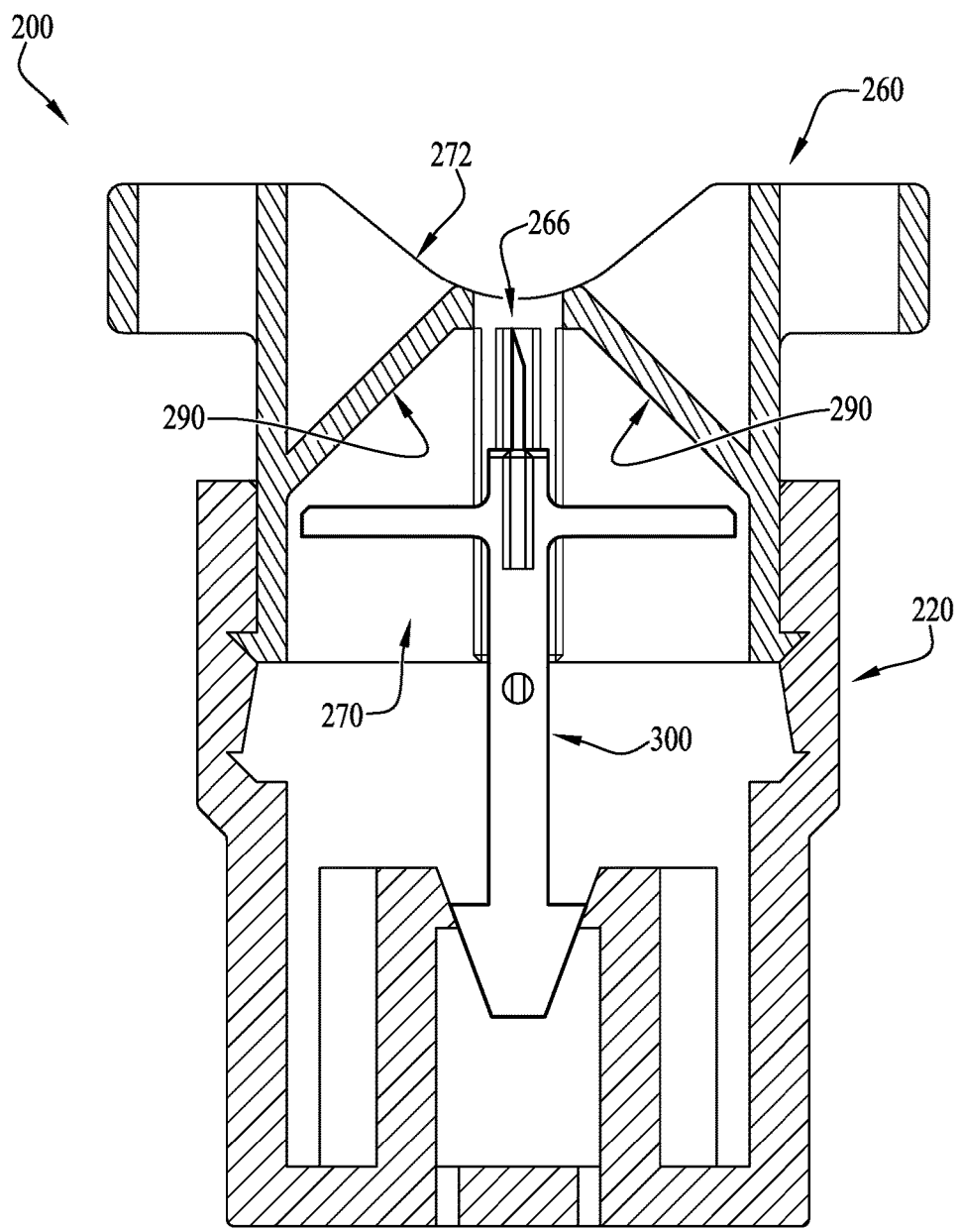
FIG. 24 is a cross-sectional view of a single-use compression lancing device according to another example embodiment of the present invention, showing a top housing having extensions formed therewith.

As shown in FIG. 21, when the top housing 60 is moved to its furthest extent within the bottom housing 20, a force caused by the compression or flexure of the arms 126 (e.g., engaging the angled internal walls 90) causes the locking feature (e.g., chamfered surfaces 122 and lips 124) to pass beyond the chamfered surfaces 44 and lips 46 of the elongate fingers 42 of the lock feature 40 of the bottom housing 20, thereby causing the lancet 100 to retract within the lancing device housings 20, 60 towards the second end 24 of the bottom housing 20 (see FIG. 22). In example forms, the force of the arms when flexed due to engagement with the angled internal walls 90 is preferably greater than the force required to prevent the locking feature of the lancet 100 from passing beyond the lock feature 40 of the bottom housing 20. Thus, the force of the flexed arms 126 preferably causes the elongate fingers 42 to generally flex outwardly to permit the locking feature of the lancet 100 to pass therethrough. Once the locking feature of the lancet 100 has passed the lock feature 40 of the bottom housing 20, the lancing device is not capable of further operation and the lancing device 10 can be discarded. In example forms, with the chamfered surfaces 80 and lips 82 of the cantilevered fingers 76 fitted within the second positional indentations 34 of the interior surface 30 of the bottom housing 20, the top housing 60 is prevented from moving relative to the bottom housing 20. Furthermore, once the locking feature of the lancet 100 has passed the lock feature 40 of the bottom housing 20, the arms 126 of the lancet 100 are preferably configured to prevent the sharp tip portion 113 of the needle 112 from protruding from the opening 66, and whereby the arms 126 are now incapable of flexing since the locking feature of the lancet 100 has moved beyond the lock feature 40.

FIGS. 24-29 show a single-use compression lancing device 200 according to an additional example embodiment of the present invention. As shown, the lancing device 200 is substantially similar to the lancing device 10 as described above. Preferably, the top housing 260 comprises a pair of handles or wings 292 generally extending transversely therefrom near the first end 262. Preferably, the handles provide an end surface 294 such that a subject or user can easily press or move the top housing 260 within the bottom housing 220. Alternatively, the handles 292 are preferably provided such that a subject can press the bottom housing 220, like a button, in a direction towards to top housing 260. In some example forms, a plurality of generally rectangular channels or openings are formed within the handle, for example, to eliminate or reduce unnecessary material costs. Preferably, a substantially arcuate or curved surface 272 is provided near the lancet opening 266, for example, to assist in the positioning of the subjects skin near the projection of the sharp tip portion of the lancet needle.

In example embodiments, the bottom housing, the top housing, and the lancet are preferably designed for manufacture using plastic injection molding with the potential for co-molded and/or adhered stainless steel lancet needles. Preferably, the size, shape and dimensions of the top and bottom housings, and the lancet, can be chosen as desired. The needle of the lancet can be formed from stainless steel, other metals, plastic or other materials. Generally, the needle is sharp and may have any number of bevels. The tip geometry may be manufactured using any process as desired. In alternative embodiments, the lancing devices 10, 200 of the present invention may be configured for multiple uses, for example, instead of a single-use application as disclosed herein.

While the invention has been described with reference to preferred and example embodiments, it will be understood by those skilled in the art that a variety of modifications, additions and deletions are within the scope of the invention, as defined by the following claims.

What is claimed is:

1. A single-use compression lancing device comprising:
a lower housing extending from a first lower housing end to a second lower housing end, the first lower housing end comprising an opening into a lower housing cavity therein, the lower housing cavity comprising an internal surface and a first locking feature, the internal surface having at least one interengagement feature formed therein,
an upper housing extending from a first upper housing end to a second upper housing end, the first upper housing end comprising a lancet opening and the second upper housing end comprising a second opening into an upper housing cavity therein, the lancet opening and the second opening being in communication with the upper housing cavity, wherein at least a portion of the upper housing cavity defines an internal surface having an angled wall generally near the lancet opening; and
a lancet comprising a main body portion extending from a first lancet end to a second lancet end, the first lancet end comprising a needle extending therefrom and the second lancet end comprising a second locking feature for interengagement with the first lock feature, and wherein at least a portion of the main body portion comprises at least one flexible arm extending therefrom for sliding interengagement with the angled wall of the upper housing
wherein the upper housing further comprises side surfaces generally near the second upper housing end thereof, and wherein at least one of the side surfaces comprises a cantilevered finger including a chamfered surface and an overhang.

2. The single-use compression lancing device of claim 1, wherein the upper housing further comprises a guidance feature for guiding the lancet along a generally axial path, the guidance feature comprising at least one ridge defining a channel formed on the internal surface of the upper housing cavity.

3. The single-use compression lancing device of claim 2, wherein the lancet further comprises at least one guide rib for traversing along the channel of the guidance feature.

4. The single-use compression lancing device of claim 1, wherein the lower housing cavity is configured for slidingly receiving the second upper housing end, and wherein the chamfered surface and overhang are configured for interengagement with the at least one interengagement feature of the internal surface of the lower housing cavity.

5. The single-use compression lancing device of claim 4, wherein the upper housing is configured to slidingly move within the lower housing, and wherein the cantilevered finger is configured to removably engage the at least one interengagement feature of the internal surface of the lower housing.

6. The single-use compression lancing device of claim 5, wherein the upper housing is movable relative to the lower housing in a first direction, but prevented from moving relative to the lower housing in a second direction, the second direction generally opposite the first direction.

* * * * *